United States Patent
Smith et al.

(10) Patent No.: US 9,554,821 B2
(45) Date of Patent: Jan. 31, 2017

(54) RESECTION DEVICE WITH SUPPORT MECHANISM AND RELATED METHODS OF USE

(71) Applicant: BOSTON SCIENTIFIC SCIMED, INC., Maple Grove, MN (US)

(72) Inventors: Paul Smith, Smithfield, RI (US); Samuel Raybin, Marlborough, MA (US); Melanie Li Sing How, Worcester, MA (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 415 days.

(21) Appl. No.: 14/207,057

(22) Filed: Mar. 12, 2014

(65) Prior Publication Data

US 2014/0276809 A1    Sep. 18, 2014

Related U.S. Application Data

(60) Provisional application No. 61/784,916, filed on Mar. 14, 2013.

(51) Int. Cl.

| A61B 18/14 | (2006.01) |
|---|---|
| A61B 17/3205 | (2006.01) |
| A61B 17/00 | (2006.01) |
| A61B 18/00 | (2006.01) |

(52) U.S. Cl.
CPC ......... *A61B 17/32056* (2013.01); *A61B 18/14* (2013.01); *A61B 2017/00269* (2013.01); *A61B 2018/00196* (2013.01); *A61B 2018/00494* (2013.01); *A61B 2018/00595* (2013.01); *A61B 2018/00601* (2013.01); *A61B 2018/00982* (2013.01); *A61B 2018/141* (2013.01); *A61B 2090/3966* (2016.02)

(58) Field of Classification Search
CPC .............. A61B 17/32056; A61B 2017/00358; A61B 17/221; A61B 2017/2212; A61B 2017/2217; A61B 2018/141
See application file for complete search history.

(56) References Cited

U.S. PATENT DOCUMENTS 5,318,564 A * 6/1994 Eggers ............... A61B 18/1233
606/47
7,806,894 B1 * 10/2010 Rosenblatt ............. A61B 18/14
606/47

(Continued)

*Primary Examiner* — Jocelyn D Ram
(74) *Attorney, Agent, or Firm* — Bookoff Andrews, PLLC (57) ABSTRACT

A medical device for resecting tissue. The medical device is slidably disposed within a working channel of an elongate introduction sheath. The medical device includes an elongate shaft having a proximal end, a distal end, and a lumen extending therebetween. The distal end of the elongate shaft may include an opening in communication with the lumen. In addition, the medical device includes a support structure having a slot extending along an inner surface of the support structure in communication with the lumen of the elongate shaft. The medical device further includes a snare loop having a first position disposed within the slot of the support structure, and a second position disposed within the lumen of the elongate shaft. An actuation member is slidably disposed within the lumen of the elongate shaft and is connected to the snare loop.

20 Claims, 3 Drawing Sheets

(56) References Cited

U.S. PATENT DOCUMENTS

| | | | |
|---|---|---|---|
| 2007/0250012 A1* | 10/2007 | Lu | A61B 17/32056 604/168.01 |
| 2008/0215064 A1* | 9/2008 | Motosugi | A61B 1/0008 606/113 |
| 2014/0276810 A1* | 9/2014 | Raybin | A61B 18/14 606/46 |
| 2014/0276814 A1* | 9/2014 | Smith | A61B 17/32056 606/49 |
| 2014/0276908 A1* | 9/2014 | Raybin | A61B 17/32056 606/113 |
| 2014/0378988 A1* | 12/2014 | Raybin | A61B 17/221 606/113 |
| 2015/0305768 A1* | 10/2015 | Harrah | A61B 17/221 606/114 |

* cited by examiner

RESECTION DEVICE WITH SUPPORT MECHANISM AND RELATED METHODS OF USE

CROSS-REFERENCE TO RELATED APPLICATIONS

This application claims the benefit of priority from U.S. Provisional Application No. 61/784,916, filed on Mar. 14, 2013, the entirety of which is incorporated by reference herein.

FIELD OF THE INVENTION

Embodiments of the present disclosure relate generally to medical devices and procedures. In particular, embodiments of the present disclosure relate to medical devices to perform tissue resection and/or retrieval during minimally invasive medical procedures.

BACKGROUND OF THE INVENTION

Tissue resection procedures, such as colonoscopy and polypectomy, are carried out by inserting introduction sheaths, such as endoscopes or laparoscopes, into the body of a patient through incisions or natural anatomical openings (e.g., oral, vaginal, and/or anal cavities). Commonly, such devices employ snares, typically designed as loops, for performing tissue resection procedures. An operator tightens the snare around the stalk (peduncle) or other tissue, thus removing it.

In a typical resection procedure, such as endoscopic mucosal resection (EMR), the submucosal layer is injected with saline to lift the mucosal layer forming a bleb. The bleb facilitates access to and visualization of the lesion. The bleb may also create a protective barrier over the muscularis layer. However, the formation of the bleb may make snaring more difficult as it increases tension in the mucosa surrounding the lesion. Further, the geometry and volume of the bleb varies based on techniques used, insertion material properties, injection speed, and lesion morphology. It may therefore be difficult to control the bleb boundaries, which can exacerbate snaring difficulties. Furthermore, snares have a tendency to slip off targeted tissue (bleb), and often require repeated efforts to capture the tissue before the resection procedures can be successfully performed.

Various methods have been developed to improve the functioning of snares. For example, one common approach is to apply a downward force on the snare in an effort to improve traction between the snare and the unwanted tissue. This downward force is usually limited due to a lack of stiffness in the snare loop, and may cause the distal end of the snare loop to deflect away from the tissue. In order to control this deflection, the downward force may continue to be applied and/or increased until the tissue is snared. Continued or increased applied force increases vulnerability of surrounding tissues towards accidental damage, as well as increases the time required to complete a procedure. In addition, it may be sometimes difficult to apply the necessary downward forces due to geometric and physical limitations such as the geometric shape of the bleb.

Therefore, there exists a need in the art for an improved snare with better capabilities, thereby allowing consistent capture, excision, and/or removal of unwanted tissue.

SUMMARY OF THE INVENTION

Embodiments of the present disclosure provide a device for resecting an undesired mass from a patient's body using a minimally invasive surgical system.

An embodiment of the disclosure includes a medical device for resecting tissue. The medical device includes an elongate shaft having a proximal end, a distal end, and a lumen extending therebetween. The distal end of the elongate shaft includes an opening in communication with the lumen. In addition, the medical device includes a support structure having a slot extending along an inner surface of the support structure in communication with the lumen of the elongate shaft. The medical device further includes a snare loop having a first position disposed within the slot of the support structure, and a second position disposed within the lumen of the elongate shaft. An actuation member is slidably disposed within the lumen of the elongate shaft and is connected to the snare loop.

Other embodiments of the disclosure disclose a medical device for resecting tissue. The medical device includes an elongate member having a distal end, a proximal end and a lumen extending therebetween. The elongate member having an opening at the distal end in communication with the lumen. The medical device includes a support structure having a slot in communication with the lumen of the elongate shaft, and a lumen formed therein. The medical device further includes a snare loop having a first position secured within the slot of the support structure, and a second position disposed within the lumen of the elongate shaft. An actuation member is slidably disposed within the lumen of the elongate shaft, the actuation member includes a distal end secured to the snare loop. Additionally, the medical device includes a plurality of guide elements having proximal portions and distal portions, the proximal portions of the guide elements extend proximally through the lumen of the elongate shaft, and the distal portions are connected to the snare loop.

Additional embodiments disclose a method for manipulating tissue. The method includes introducing a medical device within a body cavity, the medical device includes: an elongate shaft having a proximal end, a distal end, and a lumen extending therebetween, the distal end of the elongate shaft includes an opening in communication with the lumen. The medical device further includes a support structure having a slot extending along an inner surface of the support structure, the slot being in communication with the lumen of the elongate shaft. Further, the medical device includes a snare loop having a first position secured within the slot of the support structure, and a second position disposed within the lumen of the elongate shaft. The medical device includes an actuation member slidably disposed within the lumen, wherein the actuation member includes a distal end secured to the snare loop. The method further includes advancing an introduction sheath to a desired location within the body cavity and extending the snare out of the introduction sheath. The method includes placing the snare over the tissue to be resected and manipulating the tissue with the medical device.

Additional objects and advantages of the claimed disclosure will be set forth in part in the description, which follows, and in part will be understood from the description, or may be learned by practice of the disclosure. The objects and advantages of the disclosure will be realized and attained by the elements and combinations particularly pointed out in the appended claims.

It is to be understood that both the foregoing general description and the following detailed description are exemplary and explanatory only and are not restrictive of the disclosure, as claimed.

BRIEF DESCRIPTION OF THE DRAWINGS

The accompanying drawings, which are incorporated in and constitute a part of this specification, illustrate exemplary embodiments of the present disclosure and together with the description, serve to explain the principles of the disclosure.

DESCRIPTION OF THE EMBODIMENTS

Reference will now be made in detail to embodiments of the present disclosure, an example of which is illustrated in the accompanying drawings. Wherever possible, the same reference numbers will be used throughout the drawings to refer to the same or like parts. The term "distal" refers to the end farthest away from a user when introducing a device into a patient. The term, "proximal" refers to the end closest to the user when placing the device into the patient.

Overview

Embodiments of the present disclosure relate to medical devices used to retrieve and/or sever unwanted tissue. For example, embodiments of the disclosed device may facilitate removal of unwanted tissue, such as cancerous polyps or lesions, from within a patient's body, including tissue disposed on, e.g., the mucosal walls of the colon, esophagus, stomach, or duodenum. A physician may also desire to resect tissue in order to conduct a procedure such as polypectomy or mucosectomy. It should be noted that devices presented in the present disclosure could be used both for retrieving and for severing target tissue or objects. For convenience, the medical devices discussed here will be referenced as "resection devices," it being understood that such devices are equally useful for retrieving unwanted tissue.

In some embodiments, a resection device may include an elongate shaft, an outer support structure, a snare loop, an actuation element, and optional guide elements. The elongate shaft may include a lumen extending therein, an opening in communication with the lumen. The support structure may include a slot in communication with the lumen of the elongate shaft. The snare loop may have a first position disposed within the slot of the support structure, and a second position disposed within the lumen of the elongate shaft. The actuation member may be slidably disposed within the lumen, and may include a distal end secured to the snare loop.

Exemplary Embodiments

The embodiments disclosed herein are used along with an endoscopic system, which is used to introduce the disclosed embodiments to a target site within a patient's body. However, it may be noted that the embodiments of the present disclosure may be used along with other introduction devices and systems, such as trocars, catheter sheaths or the like, as well.

Figure 1:
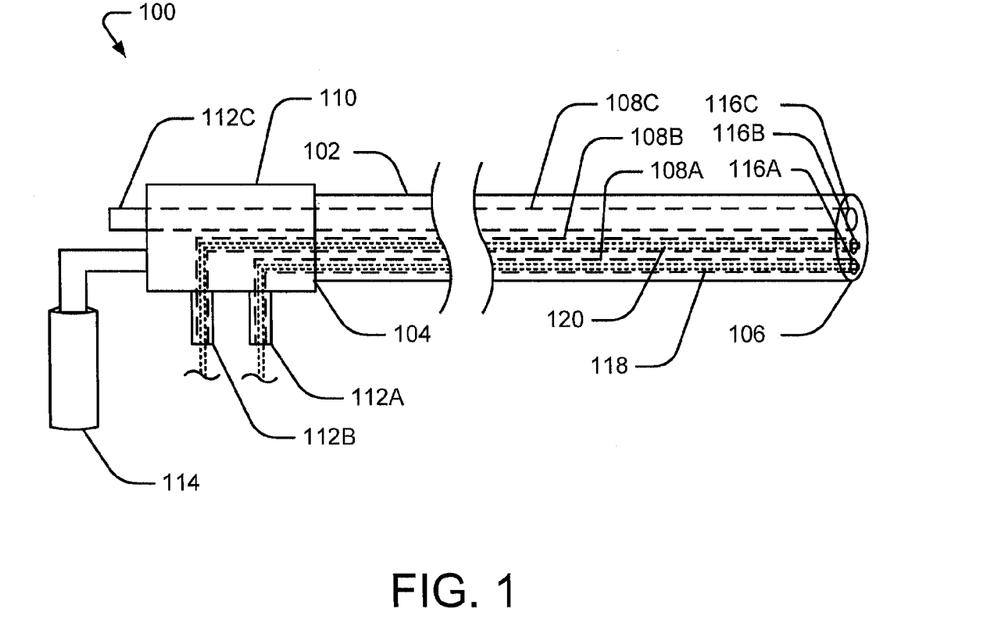
FIG. 1 illustrates an exemplary endoscopic system, according to an embodiment of the present disclosure.

FIG. 1 illustrates an exemplary endoscopic system 100. The system 100 may include an introduction sheath 102 having a proximal portion 104, a distal portion 106, and multiple working channels e.g., 108A, 108B, 108C extending therebetween. The system 100 further may include a hub assembly 110. Hub assembly 110 may be attached to the proximal portion 104 of introduction sheath 102, and may include a number of ports e.g., 112A, 112B, 112C, adapted to accommodate the introduction of a number of medical devices, as discussed in detail below. Mutually interacting attachment mechanisms (not shown), such as a Luer lock assembly, may be provided on the hub assembly 110 and introduction sheath 102, allowing those elements to be firmly joined. A handle 114 may also be provided, allowing a physician to control the operation of introduction sheath 102 and its attached devices. In some embodiments, handle 114 and hub assembly 110 may be combined into a single integral unit.

The introduction sheath 102 may be configured with appropriate length and cross-sectional dimensions to be navigated to a desired location within a patient's body. In addition, the introduction sheath 102 or a portion thereof may be steerable, which may allow the introduction sheath 102 to traverse circuitous paths within the patient's body. The channels 108A, 108B, 108C, may be configured to slidably accept one or more medical devices, communicate with the ports 112A, 112B, 112C and may have corresponding distal openings 116A, 116B, 116C allowing the medical devices to interact with the target tissue within the patient's body. An illumination device 118 and an optical device 120 may be fixedly or slidably disposed within channels 108A, 108B, respectively. For example, an illumination device 118, such as, a Xenon light source, LEDs, or the like, may provide illumination to visualize the target site with the help of optical device 120, such as a camera, a borescope, or the like. The handle 114 may facilitate an operator's manipulation of the system 100. Further, the handle 114 may include actuation elements (not shown) such as switches, knobs, gears or the like to control the movement of the introduction sheath 102 within the patient's body. The introduction sheath 102 may be introduced into a patient's body through an incision or a natural opening.

Figure 2:
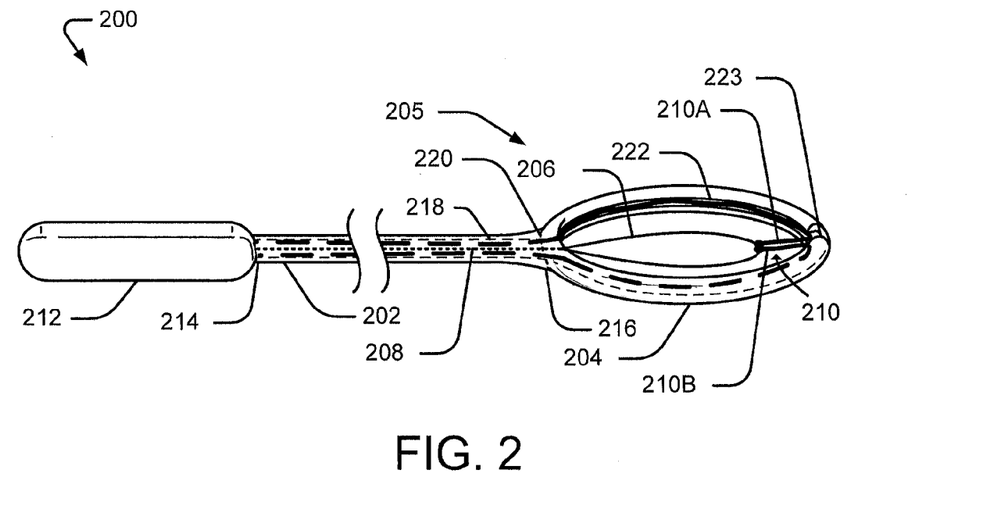
FIG. 2 depicts an exemplary resection device useable with the exemplary endoscopic system of FIG. 1, according to an embodiment of the present disclosure.

FIG. 2 depicts an exemplary resection device 200. The resection device 200 may include an elongate shaft 202, a support structure 204, and a snare assembly 205. The snare assembly 205 may include an expandable snare loop 206, an actuation member 208, a plurality of guide elements 210A, 210B, and a handle 212. The handle 212 may further include a control mechanism (not shown) at its distal end.

Resection device 200 may typically be carried within a working channel of an introduction sheath 102 (FIG. 1), such as channel 108C, during the time when the introduction sheath 102 is being navigated through a patient's body. As set out below, insertion within a working channel such as channel 108C may include some flexibility in certain portions of resection device 200. In some embodiments, the resection device 200 may be carried completely within the channel 108C.

The elongate shaft 202 may be a tubular member having a proximal end 214, a distal end 216, and a lumen 218 extending therebetween. The elongate shaft 202 may have a substantially circular cross-sectional shape. Other suitable cross-sectional shapes may be elliptical, oval, polygonal, or irregular. The cross-sectional dimensions of the elongate shaft 202 may be adapted to slidably dispose the elongate shaft 202 within channel 108C, or the lumen of any other introduction device, such as laparoscope, endoscope, trocar or the like, used along with the resection device 200. In an exemplary embodiment, if the channel 108C has a 5 F diameter, the cross-sectional dimensions of elongate shaft 202 may be less than 5 F. The elongate shaft 202 may be longer than the introduction sheath 102 (FIG. 1) to allow the operator to distally extend the elongate shaft 202 from within the channel 108C. The elongate shaft 202 may be flexible along its entire length or adapted for sufficient flexure to navigate through turns and may nonetheless have sufficient rigidity to provide the necessary force to urge the elongate shaft 202 forward. The elongate shaft 202 or a portion thereof may be selectively steerable. Actuation mechanisms (not shown) such as pull wires or other actuators may be used to selectively steer the elongate shaft 202. The lumen 218 may be sized to slidably receive the snare assembly 205 therein. The lumen 218 may communicate with an opening 220 at its distal end 216, allowing snare assembly 205 to communicate with the support structure 204, and the surrounding tissue.

The support structure 204 may be a substantially ring-shaped structure attached to the distal end 216 by a suitable attachment mechanism (not shown), such as a threaded attachment or a Luer-lock device, or support structure 204 may be integrally formed with elongate shaft 202. In some embodiments, the support structure 204 may be arcuate and may have a lumen formed therein. The shape of the support structure 204 may depend upon the geometry of the snare loop 206 (described below) in open position. For example, if the snare loop 206 is polygonal in open position, the support structure 204 may be formed having a similar polygonal geometry. The dimensions of the support structure 204 may also depend upon the size of the body cavity where the resection procedure is to be carried out and the target tissue on which the resection procedure is to be conducted. The support structure 204 may be formed of a material having sufficient flexibility to fit within a channel of introduction sheath 102, such as the channel 108C, and expand and extend therefrom.

The support structure 204 may include a slot 222 formed in its radial inward surface, in communication with the opening 220 in the elongate shaft 202. The slot 222 may be a groove or an open channel, dimensioned to receive snare loop 206. The slot 222 may be relatively wider in the portion of support structure 204 relatively nearer the elongate shaft 202, facilitating snare loop 206 sliding into the lumen 218. Similarly, the slot 222 may have a relatively larger opening 223, or through hole on the radially outward surface at the distal end of the support structure 204, adapted to receive the distal tip of the snare loop 206. In addition, the support structure 204 may contain guiding surfaces, such as chamfers, to guide the snare loop 206 into the slot 222.

Snare assembly 205 may include the snare loop 206, actuation member 208, guide elements 210, and a control mechanism. Snare loop 206 may be a loop of wire or other flexible or elongated material. In some embodiments, the snare loop 206 may be a monofilament or a wire (solid or braided), formed in a generally circular structure. Alternative suitable structures may include oval, polygonal, or other geometry. The snare loop 206 may be structured to slide between an open position, in which the shape of the snare loop 206 may be adapted to engage tissue, and a closed position, in which the snare loop 206 may be adapted to be disposed within lumen 218. The dimensions of the snare loop 206 may be adapted to the size of the tissue needed to be resected and the conditions governing the procedure, such as the size of the body cavity or the like. Further, the snare loop 206 may be configured to conduct electrical energy to carry out monopolar or bipolar cautery cutting. This procedure may aid in tissue resection and is not discussed in detail, as it is well known in the art.

Actuation member 208 may be a wire, rod, or similar elongate element shaped to facilitate deploying the snare loop 206. The distal end of the actuation member 208 may attach to the proximal end of snare loop 206 and the proximal end of the actuation member 208 may attach to the control mechanism, which may be located within the handle 212. In some embodiments, a number of elements known in the art, such as hypotubes, shafts, or the like may be used as the actuation member 208. Flexible elements may be well suited to serve as a suitable actuation member 208. It is contemplated that the actuation member 208 may be electrically conducting to transmit electrical energy to the snare loop 206 for cautery cutting.

The guide elements 210 are elongate members and may be similar to actuation member 208. The guide elements 210 may pull snare loop 206 in a direction opposite to actuation member 208 and may help position snare loop 206 within the support structure 204. A variety of elements known in the art, such as metal wires, springs, elastic fibers, plastic filaments or the like may be used as the guide elements 210. The distal portions of the guide elements 210 may connect to one or more points on the perimeter of the snare loop 206, and their proximal portions may extend proximally through the lumen in the support structure 204 and the lumen 218. The proximal portions of the guide elements 210 may be connected to an actuation element on handle 212 to be controlled by a user. It is also contemplated that guide elements 210 may be anchored to a spring, or they may be anchored and may consist of elastic materials to help bias snare loop 206 into slot 222 and the lumen within the support structure 204.

In some embodiments, as shown, the guide elements 210A and 210B may connect to the distal tip of the snare loop 206. The guide elements 210A and 210B may be disposed in opposite circumferential sides of the slot 222. The cross-sectional dimensions of the guide elements 210 may be greater than cross-sectional dimensions of the snare loop 206 wire. Slot 222 may be designed such that the guide elements 210 may not exit through the slot 222 such that they remain within the lumen of support structure 204 when snare loop 206 is deployed. For example, the slot 222 may have a wider base to accommodate the guide elements 210A and 210B and a narrow opening to prohibit the guide elements 210A and 210B from exiting the slot 222. In some embodiments, the cross-sectional shape of the slot 222 may resemble a wedge with wider dimension on radial inward surface of the support structure 204 and transition to a narrow opening, adjacent the lumen within the central region of the support structure 204. However, in some portions, such as the opening 223 as shown, the slot 222 may be widened to allow the guide elements 210A and 210B to extend out of the slot 222.

The guide elements 210 may be under tension. When the snare loop 206 is in a partially open position, the biased guide elements 210 may maintain the snare loop 206 in the plane defined by the support structure 204, which may allow the snare loop 206 gain traction and prevent the distal tip of the snare loop 206 from deflecting away from the desired tissue surface. Further, the tension within the guide elements 210 may also guide the snare loop 206 to the slot 222 when the snare loop 206 is in a fully open position.

Handle 212 may be ergonomic to allow the operator to easily hold and control the resection device 200, as well as operational elements that open and close snare loop 206. Handle 212 may embody any shapes known in the art, and in some embodiments, the handle 212 may be of a generally cylindrical shape with rounded edges. Similarly, the dimensions of the handle 212 may be adapted to facilitate the operator to hold and control the resection device 200. Within the body of handle 212, the proximal end of actuation member 208 may attach to actuation mechanism, such as control member (not shown). The control member may be switch, knob, lever, pulley, slider or the like, adapted to allow the physician to effectuate proximal and distal movement of actuation member 208. Further, in some implementations, the guide elements 210 may also be controlled proximally within the control mechanism by pulling on the guide elements 210.

A wide range of materials may be used to make the resection device 200 and its components. Suitable materials may include metals, polymers, metal-polymer composites, and the like. Some examples of suitable metals and metal alloys include stainless steel, such as 304V, 304L, and 316LV stainless steel; mild steel; nickel-titanium alloy such as linear-elastic and/or super-elastic nitinol; other nickel alloys such as nickel-chromium-molybdenum alloys (e.g., UNS: N06625 such as INCONEL® 625, UNS: N06022 such as HASTELLOY® C-22®, UNS: N10276 such as HASTELLOY® C276®, other HASTELLOY® alloys, and the like), nickel-copper alloys (e.g., UNS: N04400 such as MONEL® 400, NICKELVAC® 400, NICORROS® 400, and the like), nickel-cobalt-chromium-molybdenum alloys (e.g., UNS: R30035 such as MP35-N® and the like), nickel-molybdenum alloys (e.g., UNS: N10665 such as HASTELLOY® ALLOY B2®), other nickel-chromium alloys, other nickel-molybdenum alloys, other nickel-cobalt alloys, other nickel-iron alloys, other nickel-copper alloys, other nickel-tungsten or tungsten alloys, and the like; cobalt-chromium alloys; cobalt-chromium-molybdenum alloys (e.g., UNS: R30003 such as ELGILOY®, PHYNOX®, and the like); platinum enriched stainless steel; titanium; combinations thereof; and the like; or any other suitable material. Some examples of suitable polymers may include polytetrafluoroethylene (PTFE), ethylene tetrafluoroethylene (ETFE), fluorinated ethylene propylene (FEP), polyoxymethylene (POM, for example, DELRIN® available from DuPont), polyether block ester, polyurethane (for example, Polyurethane 85A), polypropylene (PP), polyvinylchloride (PVC), polyether-ester (for example, ARNITEL® available from DSM Engineering Plastics), ether or ester based copolymers (for example, butylene/poly(alkylene ether) phthalate and/or other polyester elastomers such as HYTREL® available from DuPont), polyamide (for example, DURETHAN® available from Bayer or CRISTAMID® available from Elf Atochem), elastomeric polyamides, block polyamide/ethers, polyether block amide (PEBA, for example available under the trade name PEBAX®), ethylene vinyl acetate copolymers (EVA), silicones, polyethylene (PE), Marlex high-density polyethylene, Marlex low-density polyethylene, linear low density polyethylene (for example REXELL®), polyester, polybutylene terephthalate (PBT), polyethylene terephthalate (PET), polytrimethylene terephthalate, polyethylene naphthalate (PEN), polyetheretherketone (PEEK), polyimide (PI), polyetherimide (PEI), polyphenylene sulfide (PPS), polyphenylene oxide (PPO), poly paraphenylene-terephthalamide (for example, KEVLAR®), polysulfone, nylon, nylon-12 (such as GRILAMID® available from EMS American Grilon), perfluoro(propyl vinyl ether) (PFA), ethylene vinyl alcohol, polyolefin, polystyrene, epoxy, polyvinylidene chloride (PVdC), poly(styrene-b-isobutylene-b-styrene) (for example, SIBS and/or SIBS 50A), polycarbonates, ionomers, biocompatible polymers, other suitable materials, or mixtures, combinations, copolymers thereof, polymer/metal composites, and the like. These are just examples and must not be seen as limiting.

The elongate shaft 202 and the support structure 204 may be made of one or more suitable polymeric or metallic materials known in the art, for example the materials discussed above. In some implementations, a combination of materials may be employed. A suitable combination material may be a polymeric material reinforced with metallic wires, braid, or springs. Another suitable combination material may include short concentric polymeric and metallic tubes joined together in an alternating fashion to form the tubular portions (elongate shaft 202 and the support structure 204). The polymeric tubes may provide flexibility, while the metallic tubes may provide rigidity to the tubular portions. Flexibility may allow the tubular portions to traverse circuitous paths, while stiffness may allow an operator to urge the tubular portions forward. Further, in some other embodiments, 3D printing techniques may be employed to make metallic or polymeric structures with desired thickness, stiffness or other desired properties.

The snare loop 206 and the actuation member 208 may be made up of suitable polymeric or metallic materials known in the art, for example the materials discussed above. In general, the snare loop 206 and the actuation member 208 may be made up of electrically conducting, biocompatible material. The electrically conducting property of the material may facilitate cautery cutting, and biocompatibility of the material may prevent any inadvertent reaction between the snare loop 206 and the surrounding tissue. Further, the material of the snare loop 206 may have suitable stiffness to resect tissue and the material of the actuation member 208 may have suitable strength to transmit force from the control mechanism to the snare loop 206.

The guide elements 210 may be made up of suitable polymeric or metallic materials known in the art, for example the materials discussed above. In general, guide elements 210 may be made of materials that may deliver tension developed within the control mechanism to the snare loop 206, for example, elastic polymers. In addition, the materials may be non-conducting to prevent electrical energy from transmitting through them during cautery cutting. This non-conducting property may prevent inadvertent damage to proximate tissue.

The handle 212 may be made of suitable polymeric or metallic materials known in the art, for example the materials discussed above. In some embodiments, a combination of materials may be employed. For example, rigid structures within the handle 212 may be made of metallic materials to provide strength and stability to the handle 212, and the flexible structures within the handle 212 may be made of polymeric materials. For example, the handle 212 may have a metallic core to provide strength, and a polymeric covering to provide a better grip for the operator.

The resection device 200 or its components may include coatings. For example, suitable low-friction material, such as TEFLON®, polyetheretherketone (PEEK), polyimide, nylon, polyethylene, or other lubricious polymer coatings may be applied over the components of the resection device 200 to facilitate their operation. For example, lubricious coatings may be applied on the elongate shaft 202 and the support structure 204 to facilitate convenient insertion through a body lumen or surgical insertion.

Further, to detect the position of elongate shaft 202 within a patient's body, at least some portions of the elongate shaft 202 and/or the support structure 204, may include radiopaque materials such as gold, palladium, platinum, tantalum, tungsten alloy, or polymeric materials loaded with radiopaque agents such as barium sulfate (BaSO$_4$) or bismuth sub carbonate ((BiO)$_2$CO$_3$). Radiopaque materials are capable of producing a relatively bright image on a fluoroscopic monitor or other imaging device.

Furthermore, the components of resection device 200 that come in contact with the patient's body may be coated with an anti-bacterial covering to inhibit bacterial growth on their surfaces. The anti-biotic coating may contain an inorganic anti-biotic agent, disposed in a polymeric matrix that may aid the antibiotic agent to adhere to the surface of the components of the resection device 200. Moreover, a drug-releasing coating may also be applied to the resection device 200 to assist in delivery of drugs to the severing site.

Figure 3A:
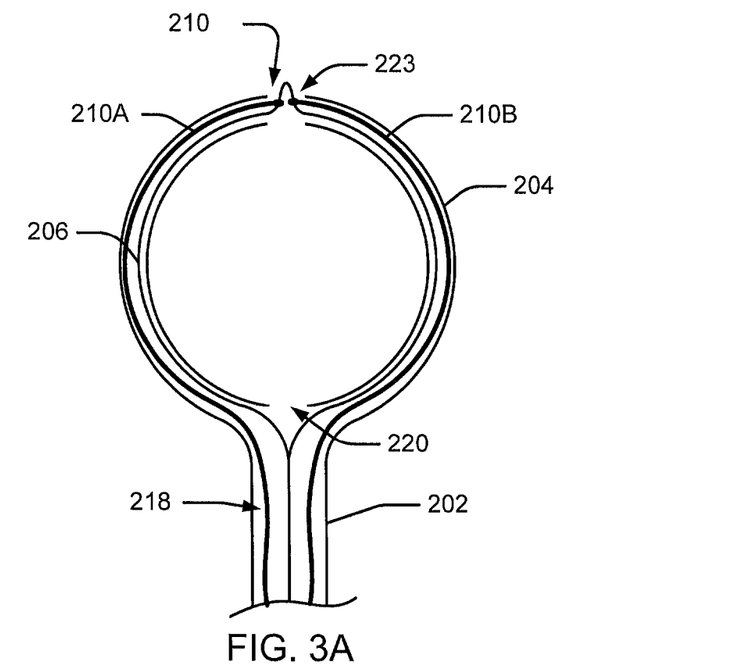
FIGS. 3A and 3B illustrate operation of the exemplary resection device of FIG. 2.
Figure 3B:
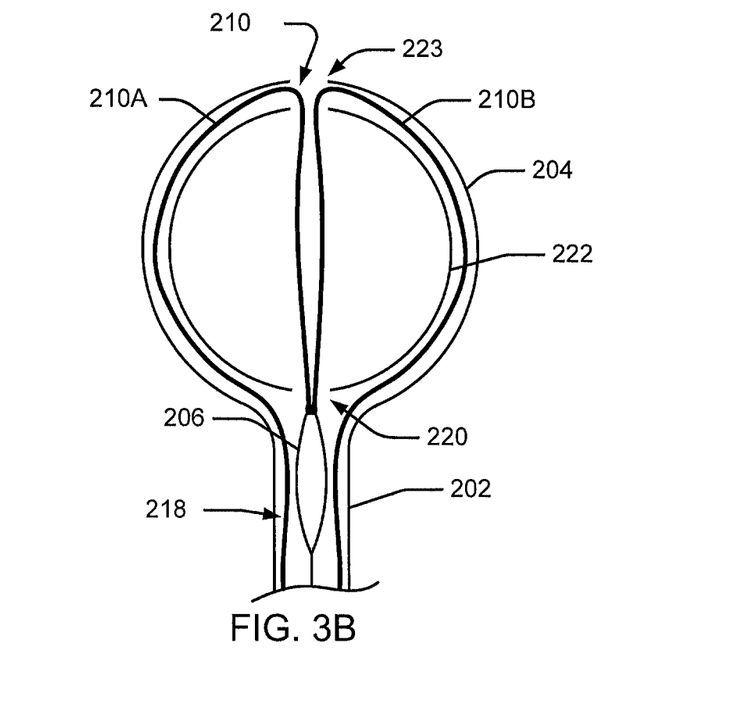

FIGS. 3A and 3B illustrate the operation of resection device 200. FIG. 3A depicts the snare loop 206 in fully open position, and FIG. 3B depicts the snare loop 206 in a fully closed position. Initially, when an operator extends the resection device 200 distally out of the channel 108C (FIG. 1), the support structure 204 expands to a deployed shaped configuration from a folded or collapsed configuration. The snare loop 206 in this stage may be in the fully open position within the slot 222, as shown in FIG. 3A. The operator may place the support structure 204 over a portion of unwanted tissue and may press the support structure 204 down on the tissue to create a bleb, or to accentuate an existing bleb, inside the perimeter of the support structure 204. In addition, before or after placing the support structure 204, the operator may inject a material into the tissue to separate tissue layers and/or partially raise a portion of tissue. The support structure 204, when placed, may create an outer boundary, may limit the diffusion of the injected material, and may help define the outer boundary of the bleb.

Once the support structure 204 is positioned, the operator may pull the actuation member 208 using the control mechanism. As the actuation member 208 is pulled, the snare loop 206 may move to a closed position and be withdrawn into lumen 218 through opening 220, as shown in FIG. 3B. During this movement from open to collapsed/closed position, the tissue within the support structure 204 may be trapped within the snare loop 206 and may be resected as the snare loop 206 is closed. Monopolar or bipolar cautery cutting techniques may facilitate this process by transmitting RF electrical energy through the collapsing snare loop 206.

As discussed, the guide elements 210 may be in tension. When the snare loop 206 starts to close, the biased guide elements 210 may facilitate retaining the snare loop 206 in the plane of the support structure 204 during the closure process. Thus, the guide elements 210 may help keep snare loop 206 engaged with tissue. In addition, the guide elements 210 may prevent the distal tip of the snare loop 206 from deflecting away from the tissue surface. Further, once the desired tissue is resected and the operator releases the actuation member 208, the guide elements 210 may pull the snare loop 206 back into the open position, guiding it back into the slot 222. Alternatively, an operator may actuate guide elements 210A, 210B to move the snare loop 206 back into the open position.

Figure 4:
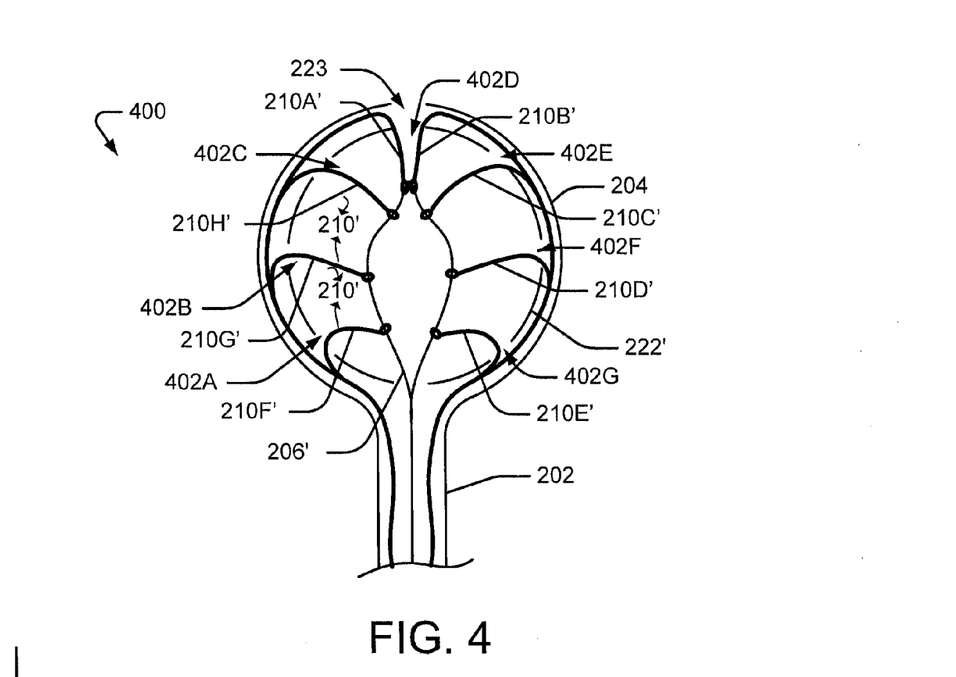
FIG. 4 illustrates an exemplary resection device, useable with the exemplary endoscopic system of FIG. 1, according to an embodiment of the disclosure.

FIG. 4 illustrates another embodiment of an exemplary support structure 400. A plurality of guide elements 210', including one or more of guide elements 210A', 210B', 210C', 210D', 210E', 210F', 210G', and 210H', may be connected to the snare loop 206' at points around its circumference in order to increase planar support during cutting, and to maintain snare loop 206' geometry as it is closed. The slot 222' may be modified to contain a plurality of holes, including one or more of 402A, 402B, 402C, 402D, 402E, 402F, and 402G, through which the guide elements 210' may be connected to the snare loop 206'.

It is also contemplated that, the cross-sectional dimensions of the guide elements 210 as shown in FIG. 4, or in FIGS. 3A and 3B, may be less than the width of the slot 222 opening. As such, straps or hooks, located within or behind the slot 222 may prevent the guide elements 210 from extending out of undesired positions.

Figure 5:
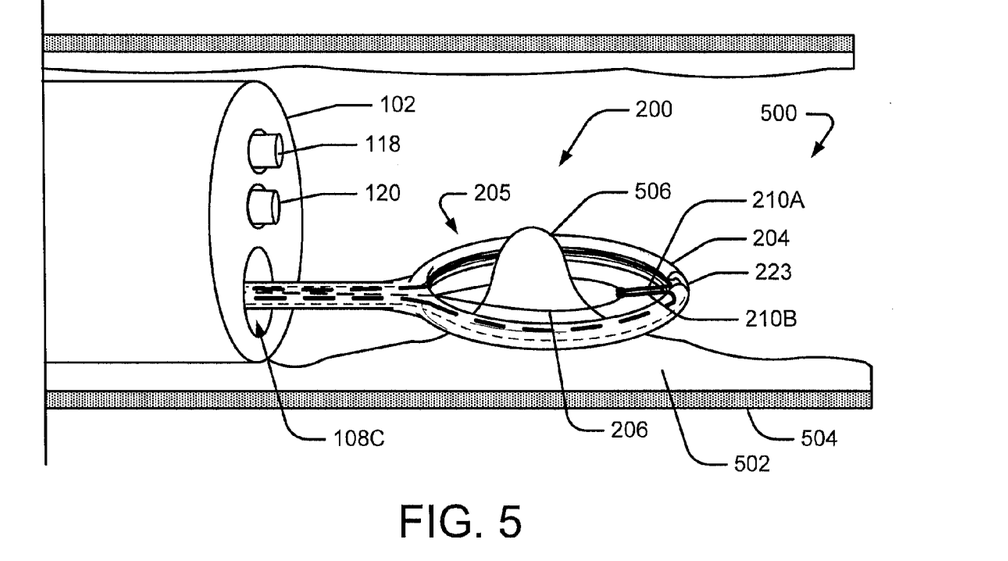
FIG. 5 depicts an exemplary method of using the devices of FIG. 2 and FIG. 4.

FIG. 5 depicts an exemplary method of use of the resection device 200 in endoscopic mucosal resection (EMR) at a target location 500 within a patient's body. The target location 500 may be a body cavity including two layers of tissue-mucosal layer 502 and muscularis layer 504. A part of mucosal layer 502 may contain cancerous polyps, lesions or other undesired tissue to be resected. An operator may insert the introduction sheath 102 within a patient's body through a small incision in the stomach, femoral vein, or a suitable artery, or through natural anatomical openings such as the mouth, nose, anus, ureter, vaginal cavity, or the like. After inserting the introduction sheath 102, the operator may maneuver the introduction sheath 102 through the patient's body to reach the target location 500. The illumination device 118 and optical/visualization device 120 may facilitate in maneuvering the introduction sheath 102 as well as during the resection procedure. Next, the operator may distally extend the resection device 200 from the introduction sheath 102 and position it over the desired tissue to be resected. The operator may then inject the desired tissue with a material using an injector device, known in the art, carried within the introduction sheath 102. Once injected, the tissue may form a bleb 506, and the support structure 204 may control the boundaries of, or accentuate the bleb 506 by pressing down around it. Once the bleb 506 is formed, the operator may resect it by shifting the snare from an open to a closed position. The bleb 506 may help in isolating the muscularis layer 504 from the resection procedure thereby reducing inadvertent damage to the muscularis layer 504. After resecting the bleb 506 or multiple blebs, the operator may then retract the resection device 200 within the introduction sheath 102, and retract the introduction sheath 102 from the patient's body. In one embodiment, multiple blebs may be resected by returning snare loop 206 to a fully open position with guide elements 210. After placement of the resection device 200, snare loop 206 may be actuated, and the guide elements 210 may help in expanding the snare loop 206 and accurate engagement of the snare loop 206 over the blebs. Once the snare loop 206 is placed, the snare loop 206 may be pressed against the tissue, increasing the bleb's penetration into the snare loop 206. After the first bleb is resected, actuation of guide elements 210A and 210B may return snare loop 206 to a fully open position, within the support structure 204. The support structure 204 can then be moved to another location and the resection procedure repeated.

Embodiments of the present disclosure may be used in any medical or non-medical procedure, including any medical procedure where appropriate. In addition, at least certain aspects of the aforementioned embodiments may be combined with other aspects of the embodiments, or removed, without departing from the scope of the disclosure.

Other embodiments of the present disclosure will be apparent to those skilled in the art from consideration of the specification and practice of the embodiments disclosed herein. It is intended that the specification and examples be considered as exemplary only, with a true scope and spirit of the disclosure being indicated by the following claims.

What is claimed is:

1. A medical device for resecting tissue comprising:
an elongate shaft having a proximal end, a distal end, and a lumen extending therebetween, wherein the distal end of the elongate shaft includes an opening in communication with the lumen;
a support structure having a slot extending along an inner surface of the support structure, the slot being in communication with the lumen of the elongate shaft;
a snare loop having a first position disposed within the slot of the support structure, and a second position disposed within the lumen of the elongate shaft;
an actuation member slidably disposed within the lumen, wherein the actuation member includes a distal end portion secured to the snare loop; and
a first guide element and a second guide element, wherein the first and second guide elements are connected to the snare loop, and wherein proximal portions of the first and second guide elements are connected to the actuation member.

2. The medical device of claim 1, wherein the support structure is attached to the distal end of the elongate shaft.

3. The medical device of claim 1, wherein the support structure includes a lumen formed therein in communication with the slot and the lumen of the elongate shaft.

4. The medical device of claim 3, wherein the first and second guide elements are disposed within the lumen of the support structure.

5. The medical device of claim 3, wherein distal portions of the first and second guide elements are connected to one or more points on the snare loop, and proximal portions of the first and second guide elements extend through the lumen in the support structure and through the lumen of the elongate shaft.

6. The medical device of claim 1, wherein the snare loop and the actuation member are configured to conduct electrical energy.

7. The medical device of claim 1, wherein a proximal portion of the actuation member includes a control mechanism.

8. The medical device of claim 1, further comprising a sheath disposed over the elongate shaft.

9. The medical device of claim 1, wherein the slot of the support structure includes a plurality of holes, through which the guide elements are connected to the snare loop.

10. The medical device of claim 1, wherein the snare loop is configured to translate between the first and second positions.

11. The medical device of claim 1, wherein the support structure is a substantially ring-shaped structure.

12. The medical device of claim 1, wherein the guide elements bias the snare loop to the slot.

13. A medical device for resecting tissue, the medical device comprising:
an elongate member having a distal end, a proximal end, and a lumen extending therebetween, the elongate member having an opening at the distal end in communication with the lumen;
a support structure having a slot in communication with the lumen of the elongate shaft, and a lumen formed therein;
a snare loop having a first position secured within the slot of the support structure, and a second position disposed within the lumen of the elongate shaft; and
an actuation member slidably disposed within the lumen of the elongate shaft, the actuation member includes a distal end secured to the snare loop; and
a plurality of guide elements having proximal portions and distal portions, the proximal portions of the guide elements extending proximally through the lumen of the elongate shaft, and the distal portions connected to the snare loop.

14. The medical device of claim 11, wherein the support structure is a substantially ring-shaped structure.

15. The medical device of claim 11, wherein the proximal portions of the guide elements extend proximally through the slot and the distal portions of the guide elements are connected to a distal tip of the snare loop.

16. The medical device of claim 11, wherein the slot of the support structure includes a plurality of holes, through which the guide elements are connected to the snare loop.

17. The medical device of claim 11, wherein the guide elements bias the snare loop to the slot.

18. The medical device of claim 13, wherein the snare loop and the actuation member are configured to conduct electrical energy.

19. A method for manipulating tissue comprising:
introducing a medical device within a body cavity, the medical device including:
an elongate shaft having a proximal end, a distal end, and a lumen extending therebetween, wherein the distal end of the elongate shaft includes an opening in communication with the lumen;
a support structure having a slot extending along an inner surface of the support structure, the slot being in communication with the lumen of the elongate shaft;
a snare loop having a first position secured within the slot of the support structure, and a second position disposed within the lumen of the elongate shaft;
an actuation member slidably disposed within the lumen, wherein the actuation member includes a distal end secured to the snare loop; and
a plurality of guide elements having proximal portions and distal portions, the proximal portions of the guide elements extending proximally through the lumen of the elongate shaft, and the distal portions of the guide elements connected to the snare loop;
advancing an introduction sheath to a desired location within the body cavity;
extending the snare loop out of the elongate sheath;
placing the snare loop over tissue targeted for resection;
manipulating the tissue with the medical device; and
actuating the guide elements in a proximal direction to transition the snare loop into the second position.

20. The method of claim 19, further comprising:
actuating the actuation member in a proximal direction to transition the snare loop into the first position to resect the tissue.

* * * * *